(12) United States Patent
Yagi et al.

(10) Patent No.: US 9,233,916 B2
(45) Date of Patent: Jan. 12, 2016

(54) METHOD FOR PRODUCING NITRILE

(71) Applicant: TAKASAGO INTERNATIONAL CORPORATION, Ota-ku, Tokyo (JP)

(72) Inventors: Kenji Yagi, Atsugi (JP); Kenya Ishida, Yokohama (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/397,224

(22) PCT Filed: May 20, 2013

(86) PCT No.: PCT/JP2013/063960
§ 371 (c)(1),
(2) Date: Oct. 27, 2014

(87) PCT Pub. No.: WO2013/176088
PCT Pub. Date: Nov. 28, 2013

(65) Prior Publication Data
US 2015/0148558 A1  May 28, 2015

(30) Foreign Application Priority Data

May 21, 2012 (JP) .................................. 2012-115488

(51) Int. Cl.
| C07C 253/00 | (2006.01) |
| C07C 253/20 | (2006.01) |
| C07C 255/07 | (2006.01) |
| B01J 27/18 | (2006.01) |
| C07C 239/10 | (2006.01) |
| C07C 255/33 | (2006.01) |

(52) U.S. Cl.
CPC ............ *C07C 253/00* (2013.01); *B01J 27/1806* (2013.01); *C07C 239/10* (2013.01); *C07C 255/07* (2013.01); *C07C 255/33* (2013.01)

(58) Field of Classification Search
CPC combination set(s) only.
See application file for complete search history.

(56) References Cited

U.S. PATENT DOCUMENTS

| 4,456,562 | A | 6/1984 | Tamura et al. |
| 5,457,222 | A | 10/1995 | Oku et al. |
| 5,514,830 | A | 5/1996 | Oku et al. |
| 6,320,067 | B1 | 11/2001 | Oku et al. |

FOREIGN PATENT DOCUMENTS

| JP | 58-96053 A | 6/1983 |
| JP | 2000-344723 A | 12/2000 |
| WO | 93/02046 A1 | 2/1993 |

OTHER PUBLICATIONS

International Searching Authority, International Search Report of PCT/JP2013/063960, dated Jul. 8, 2013. [PCT/ISA/210].

*Primary Examiner* — Nyeemah A Grazier
(74) *Attorney, Agent, or Firm* — Sughrue Mion, PLLC

(57) ABSTRACT

The present invention provides a method for producing a nitrile represented by general formula (1) (in the formula, R denotes an optionally substituted alkyl group, alkenyl group, dienyl group, aralkyl group or aryl group having a total of 3-20 carbon atoms), and the method includes heating an aldoxime represented by general formula (2) (in the formula, R denotes the same groups as those mentioned above) at 80-250° C. in the presence of an alkali metal or alkaline earth metal salt of phosphoric acid (catalyst A) and distilling off water generated as the reaction progresses to outside the reaction system.

5 Claims, No Drawings

METHOD FOR PRODUCING NITRILE

CROSS REFERENCE TO RELATED APPLICATIONS

This application is a National Stage of International Application No. PCT/JP2013/063960 filed May 20, 2013, claiming priority based on Japanese Patent Application No. 2012-115488, filed May 21, 2012, the contents of all of which are incorporated herein by reference in their entirety.

TECHNICAL FIELD

The present invention relates to a high-yield and simple method for producing a nitrile which is useful as a flavor and/or fragrance or as a starting material for organic synthesis of a flavor and/or fragrance, a pharmaceutical, or the like.

BACKGROUND ART

Several methods for obtaining the corresponding nitrile from an aldoxime using a dehydrating agent have been known. Typical examples of the methods include (A) a method in which an aldoxime is dehydrated by a reaction with an acid anhydride such as acetic anhydride, (B) a method in which an aldoxime is dehydrated with phosphonitrilic chloride (hexachlorocyclotriphosphazatriene), and (C) a method in which an aldoxime is dehydrated by a reaction with a basic compound such as an alkali metal hydroxide (WO93/02046).

However, the employment of the above-described method (A) is disadvantageous in that acetic anhydride has to be used in an equimolar amount or more to the aldoxime, and hence the starting material cost is high. In addition, the acetic anhydride is finally converted to acetic acid, and hence the waste acetic acid treatment is necessary. The employment of the method (B) is also disadvantageous in that phosphonitrilic chloride has to be used in an equimolar amount or more relative to the aldoxime, and hence the starting material cost increases, and moreover that the waste product treatment cost is not lower in this case than in the case of acetic anhydride. The employment of the method (C) is disadvantageous in that the produced nitrile compound may be converted by hydrolysis to the amide compound depending on the reaction temperature or the reaction time (see Comparative Examples 1 to 3). In this respect, a method in which an acid such as sulfuric acid is used as the dehydrating agent has been reported as a method for overcoming these disadvantages (Japanese Patent Application Publication No. Sho 58-096053). This method is better than the above-described methods, because it is only necessary to use a catalytic amount of the acid, and the amount of waste products is small. However, this method is disadvantageous because of its limited application range. Specifically, nitriles can be obtained from aromatic oximes in yields of 80% or higher, but the yields of nitriles from aliphatic oximes decrease to 70%. Hence, this method cannot be practically applied to a wide range.

SUMMARY OF INVENTION

Accordingly, an object of the present invention is to provide a method for producing a nitrile which provides a high yield, which does not require strict temperature control, and which is extremely advantageous from the viewpoint of the economy of production.

The present invention provides a method for producing a nitrile represented by general formula (1):

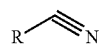  (1)

wherein R represents an alkyl, alkenyl, dienyl, aralkyl, or aryl group having 3 to 20 carbon atoms in total, which optionally has a substituent(s), the method comprising:
heating an aldoxime represented by general formula (2) to 80 to 250° C. in the presence of an alkali metal or alkaline earth metal phosphate (catalyst A):

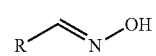  (2)

wherein R has the same meaning as above; and
distilling water, which is produced with the progress of a reaction, away from a reaction system.

DESCRIPTION OF EMBODIMENTS

Hereinafter, the present invention will be described in detail.

The present invention is represented by the following reaction formula:

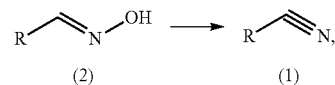

wherein R has the same meaning as above.

Specifically, a method for producing a nitrile represented by general formula (1) of the present invention comprises: heating an aldoxime represented by general formula (2) to 80 to 250° C. in the presence of an alkali metal or alkaline earth metal phosphate (catalyst A); and distilling water, which is produced with the progress of a reaction, away from a reaction system.

In the above-described general formulae (1) and (2), the group represented by R is an alkyl, alkenyl, dienyl, aralkyl, or aryl group having 3 to 20 carbon atoms in total, which optionally has a substituent(s).

The alkyl group is preferably an alkyl group having 1 to 20 carbon atoms, and more preferably an alkyl group having 5 to 14 carbon atoms. Specific examples of the alkyl group include a heptyl group, a nonyl group, an undecyl group, a lauryl group, a myristyl group, and the like.

The alkenyl group is preferably an alkenyl group having 2 to 20 carbon atoms, and more preferably an alkenyl group having 5 to 10 carbon atoms. Specific examples of the alkenyl group include a pentynyl group, a hexynyl group, a 2,6-dimethyl-5-heptenyl group, a decenyl group, and the like.

The dienyl group is preferably a dienyl group having 4 to 20 carbon atoms, and more preferably a dienyl group having 5 to 10 carbon atoms. Specific examples of the dienyl group include a 2,6-dimethyl-1,5-heptadienyl group, and the like.

The aralkyl group is preferably an aralkyl group having 7 to 20 carbon atoms, and more preferably an aralkyl group having 7 to 10 carbon atoms. Specific examples of the aralkyl group include a benzyl group, a 2-phenethyl group, a 2-styryl group, and the like.

The aryl group is preferably an aryl group having 6 to 20 carbon atoms, and more preferably an aryl group having 6 to 14 carbon atoms. Specific examples of the aryl group include a phenyl group, a methylphenyl group, a dimethylphenyl group, a naphthyl group, an anthryl group, a phenanthryl group, a biphenyl group, a tolyl group, a xylyl group, a mesityl group, a methoxyphenyl group, a dimethoxyphenyl group, a fluorophenyl group, and the like.

Meanwhile, substituents which can be present in these groups include cyano groups, hydroxyl groups, alkoxyl groups, nitro groups, alkoxycarbonyl groups, amide groups, halogen atoms, and the like. The alkoxyl groups are preferably alkoxyl groups having 1 to 20 carbon atoms, and more preferably alkoxyl groups having 1 to 6 carbon atoms. Specific examples of the alkoxyl groups include a methoxy group, an ethoxy group, a n-propoxy group, an isopropoxy group, a n-butoxy group, a 2-butoxy group, an isobutoxy group, a tert-butoxy group, a n-pentyloxy group, a 2-methylbutoxy group, a 3-methylbutoxy group, a 2,2-dimethylpropyloxy group, a n-hexyloxy group, a 2-methylpentyloxy group, a 3-methylpentyloxy group, a 4-methylpentyloxy group, a 5-methylpentyloxy group, and the like. The alkoxycarbonyl groups are preferably alkoxycarbonyl groups having 2 to 10 carbon atoms, and more preferably alkoxycarbonyl groups having 2 to 6 carbon atoms. Specific examples of the alkoxycarbonyl groups include a methoxycarbonyl group, an ethoxycarbonyl group, a n-propoxycarbonyl group, an isopropoxycarbonyl group, a n-butoxycarbonyl group, a 2-butoxycarbonyl group, an isobutoxycarbonyl group, a tert-butoxycarbonyl group, a n-pentyloxycarbonyl group, a 2-methylbutoxycarbonyl group, a 3-methylbutoxycarbonyl group, a 2,2-dimethylpropyloxycarbonyl group, a n-hexyloxycarbonyl group, a 2-methylpentyloxycarbonyl group, a 3-methylpentyloxycarbonyl group, a 4-methylpentyloxycarbonyl group, a 5-methylpentyloxycarbonyl group, and the like. The amide groups are preferably amide groups having 2 to 20 carbon atoms, and more preferably amide groups having 2 to 14 carbon atoms. Specific examples of the amide groups include a methylaminocarbonyl group, a dimethylaminocarbonyl group, a diethylaminocarbonyl group, a diisopropylaminocarbonyl group, a cyclohexylaminocarbonyl group, a phenylaminocarbonyl group, a diphenylaminocarbonyl group, a naphthylaminocarbonyl group, a phenylaminocarbonyl group, a benzylaminocarbonyl group, a dibenzylaminocarbonyl group, and the like.

The aldoxime (2), which is a starting material compound used in the method for producing a nitrile of the present invention, can be obtained by, for example, reacting the corresponding aldehyde with an inorganic salt of hydroxylamine in a usual manner.

As the catalyst A used in the production method of the present invention, one or a suitable combination of two or more selected from alkali metal phosphates and alkaline earth metal phosphates can be used. Specifically, the alkali metal phosphates and alkaline earth metal phosphates include potassium dihydrogen phosphate, dipotassium hydrogen phosphate, tripotassium phosphate, sodium dihydrogen phosphate, disodium hydrogen phosphate, trisodium phosphate, lithium dihydrogen phosphate, dilithium hydrogen phosphate, trilithium phosphate, magnesium phosphate tribasic, calcium phosphate tribasic, and the like. Of these catalysts, it is preferable to use an alkali metal phosphate in terms of the reaction yield, and it is further preferable to use tripotassium phosphate from the viewpoint of the economy of production.

In the present invention, it is preferable that the total amount of these catalysts used be 0.1 to 50% by weight, and particularly preferably 0.1 to 5% by weight, relative to the weight of the aldoxime (2), which is a starting material compound. In the present invention, the reaction temperature for obtaining the nitrile (1) from the aldoxime (2) is 80 to 200° C., and preferably 100 to 160° C.

In the present invention, processes for distilling water, which is produced with the progress of the reaction, away from the reaction system are not particularly limited, and highly efficient examples thereof include a process in which the water is removed by azeotropic distillation using a solvent which can be azeotropically distilled with water, a process in which the water is distilled away by evaporation with the pressure in the reaction system being reduced, and the like. Examples of the above-described solvent which can be azeotropically distilled with water include benzene, toluene, xylene, chlorobenzene, heptane, and the like.

In the present invention, when the above-described process in which the water is removed by azeotropic distillation using an azeotropic solvent is employed, the reaction for obtaining the nitrile (1) from the aldoxime (2) is preferably conducted under atmospheric pressure, in general. On the other hand, when the process in which a high-boiling point solvent is added, and the water is distilled away by evaporation under reduced pressure, the reaction is conducted preferably at 200 torr or below, in general, and more preferably 60 torr or below.

The nitrile (1), which is the target compound, can be isolated by purifying the thus obtained crude nitrile by distillation, column chromatography, or the like.

INDUSTRIAL APPLICABILITY

The present invention makes it possible to obtain a nitrile which is useful as a flavor and/or fragrance or as a starting material for organic synthesis of a flavor and/or fragrance, a pharmaceutical, or the like in a high yield and in an extremely advantageous manner from the viewpoint of the economy of production. Hence, it can be expected that the present invention will be widely applied to the fields of cosmetics, pharmaceuticals, and the like.

EXAMPLES

Hereinafter, the present invention will be described more specifically based on Examples. However, the present invention is not limited thereto at all.

[Measuring Instruments]

The following instruments were used for measurement of physical properties of compounds obtained in Examples.

NMR: DRX500 (manufactured by Bruker)

GC/MS: GCMS-QP2010 (manufactured by Shimadzu Corporation)

Column: RTX-1 (30 m in length×0.25 m in inner diameter, liquid phase film thickness: 0.25 µm)

Gas chromatographic purity: GC-4000 (manufactured by GL Sciences Inc.)

Column: RTX-1 (30 m in length×0.25 mm in inner diameter, liquid phase film thickness: 0.25 µm)

Temperature conditions: column: 100° C.→5° C./min→300° C.,

Injection: 250° C., Detector: 250° C. (FID)

Note that GCP represents gas chromatographic purity.

Synthesis Example 1

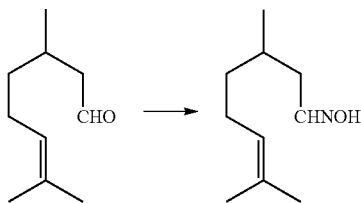

To a 3 L four-necked flask, 500 g (3.24 mol) of d-citronellal, 351 g (0.66 eq) of $(NH_4OH)_2SO_4$, and 1.5 L of water were added, and stirred at 5° C. with ice cooling. While the inside temperature was kept at 10° C. or below, 337 g (1.3 eq) of 50% aqueous NaOH was added dropwise over 3 hours. After completion of the dropwise addition, the mixture was stirred at the same temperature for 1 hour. Then, the conversion was determined to be 99% by GC, and the reaction was considered to be completed. To the reaction mixture, 250 ml of toluene was added. After stirring, the aqueous layer was removed by phase separation. The organic layer was again washed with 500 ml of water, and then the solvent was distilled away with an evaporator to obtain 543 g of a crude oxime (GCP=93.7%, yield: 99%, E: Z=1:1).

$^1$H-NMR (CDCl$_3$): δ 0.94 (d, 3H, J=6.7), 0.96 (d, 3H, J=6.7), 1.23 (m, 2H), 1.37 (m, 2H), 1.60 (s, 6H), 1.68 (s, 6H), 1.70 (m, 2H), 2.02 (m, 5H), 2.20 (dt, 1H, J=6.1, 8.2), 2.28 (m, 1H), 2.37 (dt, 1H, J=5.7, 15.9), 5.09 (m, 2H), 6.74 (t, 1H, J=5.6), 7.42 (t, 1H, J=6.5)

$^{13}$C-NMR (CDCl$_3$): δ 17.63, 19.45, 19.72, 25.41, 25.47, 25.69, 30.53, 30.92, 31.88, 36.40, 36.65, 36.84, 124.30, 124.35, 131.53, 151.63, 152.13

GC/MS (m/e): 169 (M$^+$), 152, 136, 121, 109, 95, 70, 69, 55, 41

Example 1

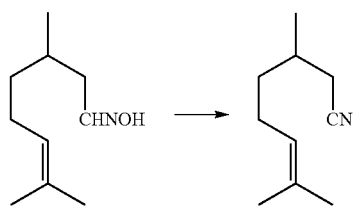

To a 3 L four-necked flask equipped with a Dean-Stark water separator, 543 g (3.2 mol) of the crude oxime obtained in Synthesis Example 1, 10.9 g (2% by weight) of K$_3$PO$_4$, and 1.6 L of xylene were added, and the mixture was heated with stirring. The mixture started to reflux at an inside temperature of 142 to 143° C., and the reflux state was kept for 2 hours (amount of water collected: 48.5 g). By GC, the conversion was determined to be 100% and the selectivity was determined to be 95%, and the reaction was considered to be completed. Here, the conversion is represented by {([weight of oxime charged]−[weight of oxime recovered])/[weight of oxime charged]}×100, and the selectivity is represented by ([number of moles of nitrile produced]/[number of moles of oxime converted])×100. The reaction mixture was cooled to room temperature, and then 543 ml of water was added. After stirring, the aqueous layer was removed by phase separation. The organic layer was again washed with 543 ml of water, and then the solvent was distilled away with an evaporator. Then, the product was purified by distillation to obtain 400.4 g of 1-citronellyl nitrile (yield: 81.7% over two steps, GCP=99.5%).

$^1$H-NMR (CDCl$_3$): δ 1.07 (d, 3H, J=6.8), 1.34 (m, 1H), 1.46 (m, 1H), 1.61 (s, 3H), 1.69 (d, 3H, J=1.0), 1.86 (m, 1H), 2.01 (m, 2H), 2.24 (dd, 1H, J=16.7, 7.0), 2.32 (dd, 1H, J=16.7, 5.6), 5.07 (m, 1H)

$^{13}$C-NMR (CDCl$_3$): δ 17.65, 19.35, 24.42, 25.24, 25.65, 29.95, 35.85, 118.83, 123.41, 132.25

GC/MS (m/e): 150 (M-H), 136, 122, 108, 94, 70, 69, 55, 41, 37

Comparative Example 1

To a 200 mL four-necked flask equipped with a Dean-Stark water separator, 50 g (295.4 mmol) of the crude oxime obtained in Synthesis Example 1, 2.0 g (4% by weight) of KOH, and 25 ml of toluene were added, and the mixture was heated with stirring. A reflux state was kept for 2 hours at an inside temperature of 110° C. Two hours later, a GC analysis was conducted. The conversion was 100%, and the selectivity was 93%.

Comparative Example 2

To a 200 mL four-necked flask equipped with a Dean-Stark water separator, 50 g (295.4 mmol) of the crude oxime obtained in Synthesis Example 1, 2.0 g (4% by weight) of KOH, and 25 ml of toluene were added, and the mixture was heated with stirring. A reflux state was kept for 3 hours at an inside temperature of 110° C. Three hours later, a GC analysis was conducted. The conversion was 100%, and the selectivity was 89%. The selectivity decreased in comparison with Comparative Example 1, because the longer reaction time led to the hydrolysis of the nitrile compound to an amide compound.

Comparative Example 3

To a 200 mL four-necked flask equipped with a Dean-Stark water separator, 50 g (295.4 mmol) of the crude oxime obtained in Synthesis Example 1, 2.0 g (4% by weight) of KOH, and 25 ml of toluene were added, and the mixture was heated with stirring. A reflux state was kept for 2 hours at an inside temperature of 120 to 124° C. Two hours later, a GC analysis was conducted. The conversion was 99%, and the selectivity was 80%. The selectivity decreased in comparison with Comparative Example 1, because the higher reaction temperature led to the hydrolysis of the nitrile compound to an amide compound.

Example 2

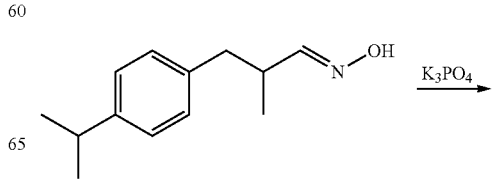

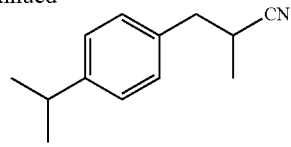

To a 3 L four-necked flask equipped with a Dean-Stark water separator, 202 g (0.98 mol) of 3-(4-isopropylphenyl)-2-methylpropanal oxime, 8 g (4% by weight) of $K_3PO_4$, and 600 mL of xylene were added, and the mixture was heated with stirring. The mixture started to reflux at an inside temperature of 138 to 140° C., and the reflux state was kept for 6 hours (amount of water collected: 12.5 g). By GC, the conversion was determined to be 99% and the selectivity was determined to be 88%, and the reaction was considered to be completed. The reaction mixture was cooled to room temperature, and then 200 ml of water was added thereto. After stirring, the aqueous layer was removed by phase separation. The organic layer was again washed with 200 ml of water. Then, the solvent was distilled away with an evaporator, and then the product was purified by distillation to obtain the nitrile (yield: 870).

$^1$H-NMR (CDCl$_3$): δ 1.24 (d, 6H, J=7.0), 1.32 (d, 3H, J=6.9), 2.81 (m, 2H), 2.906 (m, 2H), 7.15 (m, 2H), 7.19 (m, 2H)

$^{13}$C-NMR (CDCl$_3$): δ 17.61, 23.94, 27.55, 33.72, 39.61, 122.66, 126.73, 128.95, 134.14, 147.83

GC/MS (m/e): 187 (M$^+$), 172, 155, 145, 133, 117, 105, 91, 77, 65, 51, 41

Example 3

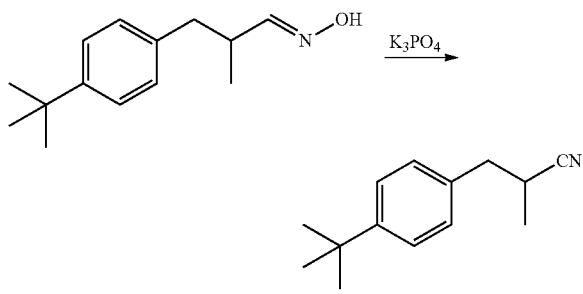

To a 3 L four-necked flask equipped with a Dean-Stark water separator, 202 g (0.92 mol) of 3-(4-tert-butylphenyl)-2-methylpropanal oxime, 8 g (4% by weight) of $K_3PO_4$, and 600 mL of xylene were added, and the mixture was heated with stirring. The mixture started to reflux at an inside temperature of 138 to 140° C., and the reflux state was kept for 6 hours (amount of water collected: 12.2 g). By GC, the conversion was determined to be 99% and the selectivity was determined to be 91%, and the reaction was considered to be completed. The reaction mixture was cooled to room temperature, and then 200 ml of water was added. After stirring, the aqueous layer was removed by phase separation. The organic layer was again washed with 200 ml of water. Then, the solvent was distilled away with an evaporator, and the product was purified by distillation to obtain the nitrile (yield: 90%).

$^1$H-NMR (CDCl$_3$): δ 1.31 (s, 9H), 1.32 (d, 3H, J=6.8), 2.81 (m, 2H), 2.91 (m, 1H), 7.16 (m, 2H), 7.35 (m, 2H)

$^{13}$C-NMR (CDCl$_3$): δ 17.62, 27.49, 31.29, 34.42, 39.48, 122.65, 125.55, 128.68, 133.76, 150.07

GC/MS (m/e): 201 (M$_+$), 186, 169, 159, 147, 131, 117, 105, 91, 77, 65, 44, 41

The invention claimed is:

1. A method for producing a nitrile of general formula (1):

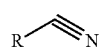

wherein R represents an alkyl, alkenyl, dienyl, aralkyl, or aryl group having 3 to 20 carbon atoms in total, which optionally has a substituent(s), the method comprising: heating an aldoxime of general formula (2) to 80 to 250° C. in the presence of an alkali metal or alkaline earth metal phosphate (catalyst A):

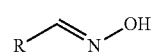

wherein R has the same meaning as above; and
distilling water, which is produced with the progress of a reaction, away from a reaction system.

2. The method for producing a nitrile according to claim 1, wherein
the catalyst A is $K_3PO_4$.

3. The method for producing a nitrile according to claim 1, wherein
the amount of the catalyst A used is 0.1 to 50% by weight relative to the aldoxime.

4. The method for producing a nitrile according to claim 1, wherein
the process for distilling the water, which is produced with the progress of the reaction, away from the reaction system is azeotropic distillation using a solvent which can be azeotropically distilled with water.

5. The method for producing a nitrile according to any claim 1, wherein
the process for distilling the water, which is produced with the progress of the reaction, away from the reaction system is evaporation with the pressure in the reaction system being reduced.

* * * * *